United States Patent [19]

Gopalkrishnan et al.

[11] Patent Number: 5,709,852
[45] Date of Patent: Jan. 20, 1998

[54] ETHYLENE OXIDE/PROPYLENE OXIDE/ ETHYLENE OXIDE (EO/PO/EO) TRIBLOCK COPOLYMER CARRIER BLENDS

[75] Inventors: Sridhar Gopalkrishnan, Woodhaven, Mich.; Richard J. Holland, Flanders; John J. Burke, Lake Mohawk, both of N.J.; Kathleen M. Guiney, Wyandotte, Mich.

[73] Assignee: BASF Corporation, Mount Olive, N.J.

[21] Appl. No.: 568,604

[22] Filed: Dec. 5, 1995

[51] Int. Cl.$^6$ .................................................. A61K 31/74
[52] U.S. Cl. .................... 424/78.08; 424/68; 424/401; 424/65; 424/49
[58] Field of Search ................... 424/78.08, 68, 424/401, 65, 49

[56] References Cited

U.S. PATENT DOCUMENTS

| | | |
|---|---|---|
| 3,740,421 | 6/1973 | Schmolka . |
| 3,867,533 | 2/1975 | Schmolka . |
| 3,997,458 | 12/1976 | Kurtz . |
| 4,382,078 | 5/1983 | Berkhoff et al. . |
| 4,465,663 | 8/1984 | Schmolka . |
| 4,476,107 | 10/1984 | Schmolka . |
| 5,035,880 | 7/1991 | Mori et al. . |
| 5,057,307 | 10/1991 | Hill et al. . |
| 5,073,368 | 12/1991 | Subramanian . |
| 5,096,698 | 3/1992 | Mitchell et al. . |
| 5,256,396 | 10/1993 | Piechota, Jr. . |
| 5,374,368 | 12/1994 | Hauschild . |
| 5,405,605 | 4/1995 | Shin .............................. 424/68 |

FOREIGN PATENT DOCUMENTS

| | | |
|---|---|---|
| 0 546 627 A1 | 6/1993 | European Pat. Off. . |
| 0 551 626 A1 | 7/1993 | European Pat. Off. . |
| WO 95/01155 | 1/1995 | WIPO . |

*Primary Examiner*—Thurman K. Page
*Assistant Examiner*—P. Kulkosky
*Attorney, Agent, or Firm*—Joanne P. Will

[57] ABSTRACT

A stable non-aqueous carrier for personal care compositions comprising:
a) about 80–98% by weight of a non-ionic liquid triblock EO/PO/EO copolymer of MW=1000–5000;
b) about 2–20% by weight of a non-ionic solid triblock EO/PO/EO copolymer of MW=4000–16,000.

6 Claims, No Drawings

ETHYLENE OXIDE/PROPYLENE OXIDE/ETHYLENE OXIDE (EO/PO/EO) TRIBLOCK COPOLYMER CARRIER BLENDS

FIELD OF THE INVENTION

The present invention relates to stable non-aqueous liquid and solid ethylene oxide/propylene oxide/ethylene oxide (EO/PO/EO) triblock copolymer blends useful as carriers for personal care products wherein said carrier comprises approximately 15–85% of said personal care product.

BACKGROUND

Non aqueous personal care compositions typically contain major amounts of a non-aqueous carrier which provides a suitable matrix into which the active ingredients, and other functional ingredients are added to form a personal care product that is easy to use. It is known in the art that the non-aqueous carrier can be composed of a blend of liquid component(s) and solid component(s) to provide a stable suspension during the formulation of said personal care compositions. For example, the liquid components in a toothpaste formula are polyethylene glycol polymers of low molecular weight, typically in the range of 200–400. Other liquid components, such as glycerol, or polypropylene glycol can also be used. The solid component which is usually added to modify the theology of the composition can be a higher molecular weight polyethylene glycol of molecular weights between 1,000–10,000. The solid component can also be a nonionic surfactant, such as a triblock copolymer of ethylene oxide/propylene oxide/ethylene oxide (EO/PO/EO). Said solid nonionic surfactant typically consists of 80% ethylene oxide and has a molecular weight usually greater than about 10,000.

Further, personal care products, such as toothpastes, mouthwashes, cosmetic creams, gels and lotions, antiperspirants, deodorants, and over-the-counter medicaments such as salves and ointments, are subject to freeze-thaw cycles during shipment and storage. Subjecting personal care products to several freeze thaw cycles can alter the rheology of the product, creating a product dispensing problem when the product becomes too hard or too soft or too viscous, and hence, difficult to use.

The art has attempted to solve this stability problem in personal care products. To this end, the art has experimented with either EO/PO/EO solid or liquid triblock copolymers in personal care products. Specifically, WO 95/01155, discloses the use of a non-ionic surfactant as a stabilizing agent in antibody containing oral compositions at levels of 0.01–6% by weight of the oral composition. Preferred non-ionic surfactants are the solid EO/PO/EO triblock copolymers known as PLURONIC® F 68, F 88 and F 108. U.S. Pat. No. 5,374,368 describes the use of liquid EO/PO/EO triblock co-polymers (PLURONIC® L 31 and L 35) in stable hydrogen peroxide releasing dental care compositions at levels of 55–90% by weight of the dental care composition. U.S. Pat. No. 3,740,421 discloses gel forming solid EO/PO/EO triblock copolymers useful in cosmetic and personal care formulations at levels of approximately 20–25% by weight. Preferred solid EO/PO/EO triblock copolymers have a molecular weight of 4,600–16,000. Said solid EO/PO/EO triblock copolymers form a gel when added to an aqueous solution. U.S. Pat. No. 3,867,533 discloses aqueous gel compositions containing solid EO/PO/EO triblock copolymers, having a molecular weight of 6,450–20,000 useful at levels of approximately 20% by weight. Said compositions are useful in preparing cosmetic formulations. U.S. Pat. No. 3,997,458 discloses solid triblock co-polymers of EO/PO/EO useful in wound cleansing compositions at levels of approximately 10% by weight. Said EO/PO/EO copolymers have a molecular weight of 5,000–13,500 (e.g., PLURONIC® F 98, F 108—available from BASF Corporation, Mt. Olive, N.J.). U.S. Pat No. 4,382,078 discloses water based aerosol compositions containing a dimethylether propellant and solid EO/PO/EO triblock copolymers at levels of 1–6% by weight. U.S. Pat. No. 4,465,663 discloses clear aqueous cosmetic gels containing solid EO/BO(butylene oxide)/EO triblock copolymers at levels of approximately 20%. U.S. Pat. No. 5,035,880 discloses a stable dentrifice compositions containing a cetylpyridinium bactericide and EO/PO/EO solid triblock copolymers (PLURONIC® F 127), and polyethylene glycol at levels of 15–80% by weight. U.S. Pat. No. 4,476,107 discloses a mouthwash containing EO/BO(butylene oxide)/EO triblock copolymers at levels of 0.5–5.0% by weight. U.S. Pat. No. 5,057,307 discloses oral hygiene gels containing non-ionic surfactants, coating substances; and viscosifiers. Said non-ionic surfactants are PLURONIC® F 108 and F 127 available from BASF Corporation, Mt. Olive, N.J. U.S. Pat. No. 5,256,396 discloses a topical composition comprising an EO/PO/EO solid triblock copolymer (PLURONIC® F 127) used at a level of more than 10% to about 17% by weight. EPO-546-627A discloses mouthwash compositions comprising solid EO/PO/EO triblock copolymers such as PLURONIC® L 108, 88 at levels of 0.5–3% by weight. EP 0-551-626 discloses a thermoreversible pharmaceutical gel comprising solid EO/PO/EO triblock copolymer such as PLURONIC® F 127 at a level of 10 to 30% by weight. U.S. Pat. No. 5,073,368 discloses mouthwashes containing solid EO/PO/EO triblock copolymers such as PLURONIC® F 87 at levels of 0.1–3% by weight. W 0 93/13750 discloses an ocular cleansing composition comprising solid PLURONIC® P 85 and paste PLURONIC® F 87 EO/PO/EO triblock copolymers. PLURONIC® P 85 is 4–9% by weight of the cleansing composition. PLURONIC® F 87 is 0.5–2% by weight of the cleansing composition. Finally, U.S. Pat. No. 5,096,698 discloses a dental creme composition containing a non-ionic triblock liquid EO/PO/EO copolymer or a solid triblock EO/PO/EO copolymer at levels of 0.1–5% by weight. Said copolymers help to prevent phase separation. PLURONIC® F 108 (solid) is most preferred, followed by PLURONIC® F 87, PLURONIC® F 127, and PLURONIC® L 72. Liquid and solid PLURONIC® surfactants are not used together in said dental creme composition.

However, the art does not disclose a blend of liquid and solid EO/PO/EO triblock copolymers, as stable non-aqueous carrier blends for personal care compositions. Applicants have surprisingly discovered that blends of liquid and solid EO/PO/EO triblock copolymers improve the freeze-thaw stability and provide adequate thermal stability for personal care products.

SUMMARY

A stable non-aqueous carrier for personal care compositions comprising:

a) about 80–93% by weight of a non-ionic liquid triblock EO/PO/EO copolymer of molecular weight (MW) 1000–5000;

b) about 2–20% by weight of a non-ionic solid triblock EO/PO/EO copolymer of molecular weight (MW) 4000–16,000.

DETAILED DESCRIPTION

A stable non-aqueous carrier for personal care compositions comprising:

a) about 80–98% by weight of a non-ionic liquid triblock EO/PO/EO copolymer of MW 1000–5000;

b) about 2–20% by weight of a non-ionic solid triblock EO/PO/EO copolymer of MW 4000–16,000.

The Non-Ionic Liquid Triblock EO/PO/EO Copolymer of MW 1000–5000

The non-ionic liquid triblock EO/PO/EO copolymers of molecular weight 1000–5000, of the present invention, are represented by the formula:

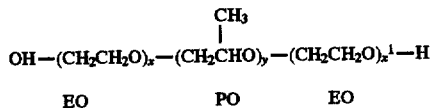
EO  PO  EO wherein x and $x^1$ and y are integers not equal to zero; x and $x^1$ represent the combined average molecular weight of the EO block in said liquid triblock copolymer; y represents the average molecular weight of the PO block in said liquid triblock copolymer.

Preferably, the molecular weight (MW) is 1000 to 3500; more preferably, the molecular weight is 1500–2800; most preferably, the molecular weight is 2200.

Preferred liquid EO/PO/EO triblock copolymers useful in the practice of the present invention are:

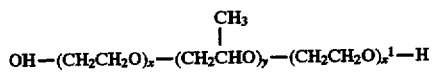

wherein $x+x^1=550$; $y=450$; molecular weight=1000.

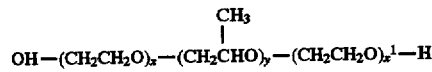

wherein $x+x^1=874$; $y=2726$; molecular weight=3600.
More preferred liquid EO/PO/EO triblock copolymers are:

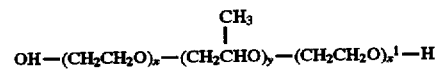

wherein $x+x^1=500$; $y=1000$; molecular weight=1500.

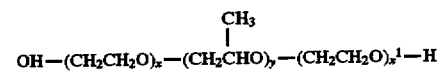

wherein $x+x^1=400$; $y=2400$; molecular weight=2800.
Most preferred liquid EO/PO/EO triblock copolymers are:

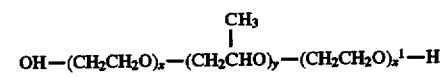

wherein $x+x^1=980$; $y=1220$; molecular weight=2200.

The Non-Ionic Solid Triblock EO/PO/EO Copolymer of MW 4,000–16,000

The solid EO/PO/EO triblock copolymers of MW 4000–16,000 are represented by the formula:

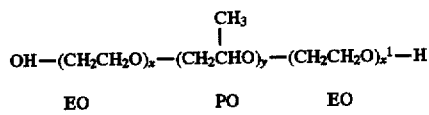
EO  PO  EO wherein x and $x^1$ and y are integers not equal to zero; x and $x^1$ represent the combined average molecular weight of the EO block in said solid triblock copolymer; y represents the average molecular weight of the PO block in said solid triblock copolymer.

Preferably, the molecular weight=4,000–16,000; more preferably, the molecular weight=10,000–15,000; most preferably, the molecular weight 13,000–14,600.

Preferred solid EO/PO/EO triblock copolymers useful in the practice of the present invention are:

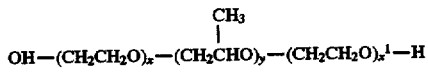

wherein $x+x^1=4000$; $y=1000$; molecular weight=5,000.

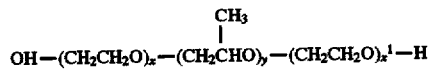

wherein $x+x^1=11,200$; $y=4,800$; molecular weight=16,000.
More preferred solid EO/PO/EO triblock copolymers are:

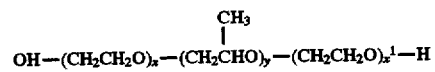

wherein $x+x^1=8500$; $y=1500$; molecular weight=10,000.

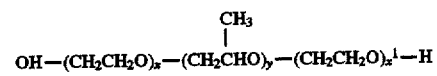

wherein $x+x^1=10,500$; $y=4,500$; molecular weight=15,000.
Most preferred solid EO/PO/EO triblock copolymers are:

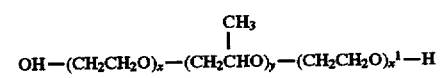

wherein $x+x^1=10,400$; $y=2,600$; molecular weight=13,000.

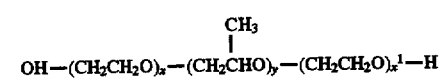

wherein $x+x^1=11,680$; $y=2,920$; molecular weight=14,600.

Preparation of the Stable Non-Aqueous Carrier Blends of the Present Invention The stable non-aqueous carrier blends useful in personal care compositions are prepared by blending the liquid triblock EO/PO/EO copolymer with the solid triblock EO/PO/EO copolymer. Preferably, 80–98% by weight of the liquid triblock copolymer is blended with 2–20% of the solid triblock copolymer. More preferably, 85–95% by weight of the liquid triblock copolymer is blended with 5–15% of the solid triblock copolymer. Most preferably, 88–92% of the liquid triblock copolymer is blended with 8–12% of the solid triblock copolymer.

Preparation of Personal Care Compositions Containing the Stable Non-Aqueous Carrier Blends of the Present Invention Personal care compositions comprising these stable non-aqueous carrier blends, prepared as described hereinabove, preferably contain 10–90% by weight of the stable non-aqueous carrier blends of the present invention; more preferably 25–85%; most preferably, 40–80% by weight of the said carrier blend in the personal care formulation in which said stable carrier is used.

Personal care formulations comprising these stable non-aqueous carrier blends may further contain other ingredients such as surfactants selected from anionic surfactants, such as sodium lauryl sulphate; sodium alkyl glyceryl ether sulfonate; alkyl benzene sulfonates. Further, small amounts of cationic surfactants,having a quaternary nitrogen, which show compatibility with the nonionic carrier blends of this invention can also be used. Various other materials may also be used in the formulating of personal care products. For example, in a dentrifice, dental abrasives consisting of freely divided silica, or calcium carbonate, calcium pyrophosphate, and hydrated alumina are added for polishing performance. Additionally, thickening agents such as xanthan gum, gum arabic, hydroxyethylcellulose can also be used to provide sufficient thickening consistency to the formulation. Also, flavoring agents such as peppermint, spearmint oils or preservatives, opacifying agents, buffer salts, sweeteners, anti-bacterial agents or anti-plaque agents, anti-inflammatory agents, anti-caries agents such as the fluoride salts can also be included in small amounts. Polymeric agents which accelerate the transport of active materials can also be included. Also, in cosmetic creams emollients such as glycerin, mineral oil and petrolatum can be added.

Personal care products are formulated according to methods known to those skilled in the art. Representative personal care product formulations are disclosed in: *Cosmetics, Science and Technology*, 2nd Edition, Vol. 1, Edited by M.S. Balsam, et al., and *A Formulary of Cosmetic Preparations*, Michael and Irene Ash, Chemical Publishing, N.Y., N.Y., both incorporated by reference herein.

The following non-limiting Examples serve to illustrate the utility of the present invention. All percentages are weight percent (%) of the total composition unless otherwise indicated.

Dentrifice Composition:

| | |
|---|---|
| 10 to 55% | abrasive, selected from the group including, but not limited to, anhydrous dicalcium phosphate, calcium carbonate, calcium pyrophosphate. |
| 0.2 to 0.8% | stannous fluoride, sodium monofluorophosphate |
| 2 to 10% | binders, including, but not limited to, gum karaya, tragacanth USP, sodium alginate; Irish moss and methyl cellulose. |
| 2 to 8% | surfactants, including, but not limited to, sodium lauryl sulfate, sodium-N-lauryl sarcosinate; dioctyl sodium sulfosuccinate. |
| 10 to 50% | humectants, including, but not limited to, glycerin; propylene glycol; sorbitol; polyethylene glycol. |
| 25 to 85% | non-aqueous carrier blend of the present invention comprising: <br> i) about 80–98% by weight of a non-ionic liquid triblock EO/PO/EO copolymer of MW 1000–5000; <br> ii) about 2–20% by weight of a non-ionic solid triblock EO/PO/EO copolymer of MW 4000–16,000 |

Body Wash Composition:

| | |
|---|---|
| 1 to 5% | emollients, including, but not limited to, lanolin, sterols (cholesterol) and fatty acids. |
| 0.1 to 3% | barrier agents, including but not limited to, petrolatum, beeswax; casein. |
| 0.01 to 0.1% | healing agents, including, but not limited to, allantoin and urea. |
| 2 to 20% | humectants, including, but not limited to, glycerin; propyleneglycol; sorbitol; polyethylene glycol. |
| 0.01 to 1% | thickeners, including but not limited to, guar gum, cellulose derivatives and Irish moss. |
| 0.5 to 3% | emulsifiers, including but not limited to, cetyl pyridinium chloride; polyoxyethylene lauryl alcohol. |
| 25 to 85% | non-aqueous carrier blend comprising: <br> i) about 80–98% by weight of a non-ionic liquid triblock EO/PO/EO copolymer of MW 1000–5000; <br> ii) about 2–20% by weight of a non-ionic solid triblock EO/PO/EO copolymer of MW 4000–16,000 |

Antiperspirant Deodorant Composition:

| | |
|---|---|
| 36 to 50% | aluminum chlorhydrate or |
| 1 to 15% | zinc oxide or |
| 1 to 15% | boric acid |
| 25 to 40% | non-aqueous carrier blend comprising: <br> i) about 80–98% by weight of a non-ionic liquid triblock EO/PO/EO copolymer of MW 1000–5000; <br> ii) about 2–20% by weight of a non-ionic solid triblock EO/PO/EO copolymer of MW 4000–16,000 |
| 25 to 50% | SD alcohol (40) |

Antiperspirant compositions may also contain emollients and perfume.

We claim:

1. A stable non-aqueous carrier for personal care compositions comprising:

a. 88–92% of a liquid EO/PO/EO triblock copolymer having the Formula:

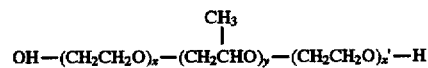

wherein x+x'=500; y=1,000; molecular weight=1,500;

b. 8–12% of a solid EO/PO/EO triblock copolymer having the Formula:

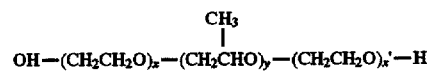

wherein x+x'=7,000; y=3,000; molecular weight=10,000.

2. A stable non-aqueous carrier for personal care compositions comprising:

a. 88–92% of a liquid EO/PO/EO triblock copolymer having the Formula:

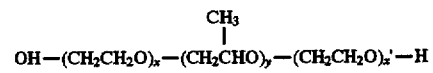

wherein x+x'=400; y=1,800; molecular weight=2,200;

b. 12% of a solid EO/PO/EO triblock copolymer having the Formula:

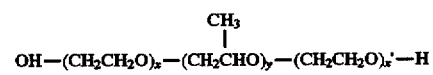

wherein x+x'=10,400; y=2,600; molecular weight=13,000.

3. A stable non-aqueous carrier for personal care compositions comprising:

a. 88–92% of a liquid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=400; y=2,400; molecular weight=2,800;

b. 8-12% of a solid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=11,680; y=2,920; molecular weight=14,600.

4. A stable non-aqueous carrier for personal care compositions comprising:

a. 88-92% of a liquid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=400; y=1,800; and the molecular weight=2,200;

b. 8-12% of a solid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=7,000; y=3,000; molecular weight=10,000.

5. A stable non-aqueous carrier for personal care compositions comprising:

a. 88-92% of a liquid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=400; y=1,800; molecular weight=2,200;

b. 8-12% of a solid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=11,680; y=2,920; molecular weight=14,600.

6. A stable non-aqueous carrier for personal care compositions comprising:

a. 88-92% of a liquid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=400; y=1,800; molecular weight=2,200;

b. 8-12% of a solid EO/PO/EO triblock copolymer having the Formula:

$$OH-(CH_2CH_2O)_x-(CH_2\underset{|}{\overset{CH_3}{C}}HO)_y-(CH_2CH_2O)_{x'}-H$$

wherein x+x'=10,400; y=2,600; molecular weight=13,000.

* * * * *